United States Patent [19]

Lee et al.

[11] Patent Number: 4,740,170

[45] Date of Patent: Apr. 26, 1988

[54] REMOVABLE SLEEVE ADAPTOR FOR ELECTRODE LEADS

[75] Inventors: Jonathan Lee, North Wahroonga; Zoran Milijasevic, Elanora Heights; Akira Nakazawa, Balmain, all of Australia

[73] Assignee: Teletronics N.V., Netherlands Antilles

[21] Appl. No.: 855,914

[22] Filed: Apr. 25, 1986

[51] Int. Cl.⁴ .......................................... H01R 33/94
[52] U.S. Cl. ................................... 439/177; 439/750
[58] Field of Search .............. 339/31 R, 31 M, 32 R, 339/32 M, 206 R, 206 P; 439/177, 217, 518, 738, 750

[56] References Cited

U.S. PATENT DOCUMENTS

| | | | |
|---|---|---|---|
| 2,692,979 | 10/1954 | Withey, Jr. | 339/31 R |
| 3,799,168 | 3/1974 | Peters | 339/31 R |
| 4,027,678 | 6/1977 | van Oostveen et al. | 128/419 P |
| 4,278,093 | 7/1981 | Lafortune et al. | 439/815 |
| 4,367,001 | 1/1983 | Munakata | 339/31 R |
| 4,583,543 | 4/1986 | Peers-Trevarton | 128/419 P |

FOREIGN PATENT DOCUMENTS 3306115 8/1984 Fed. Rep. of Germany .
2406994 5/1979 France .

*Primary Examiner*—Gil Weidenfeld
*Assistant Examiner*—Daniel W. Howell
*Attorney, Agent, or Firm*—Finnegan, Henderson, Farabow, Garrett & Dunner

[57] ABSTRACT

A removable adaptor sleeve for connecting an electrode lead having a low profile plug to a pulse generator having a high profile socket. The adaptor sleeve fits over the plug end of the electrode lead so as to provide a high profile plug configuration. The sleeve has a side wall which includes axial grooves terminating at the apex of corresponding V-shaped notches. The notches and axial grooves allow the adaptor sleeve to be torn away so as to expose for use the low profile plug end of the electrode lead, as desired.

16 Claims, 4 Drawing Sheets

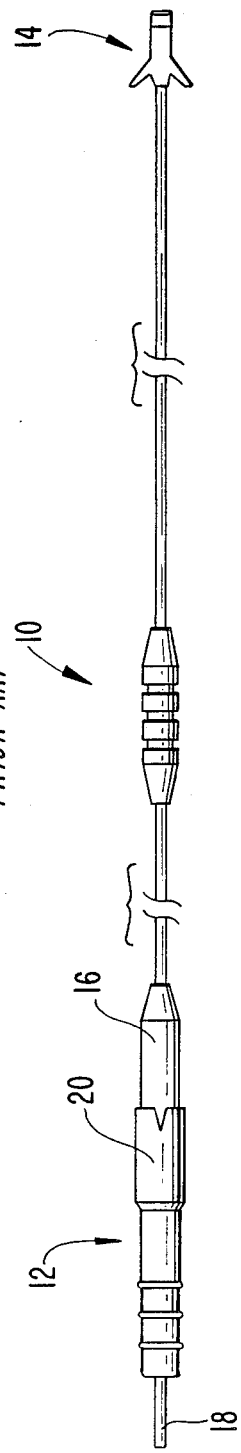
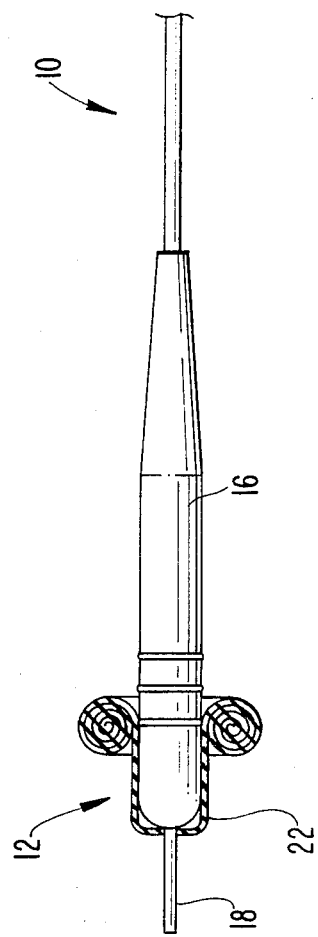
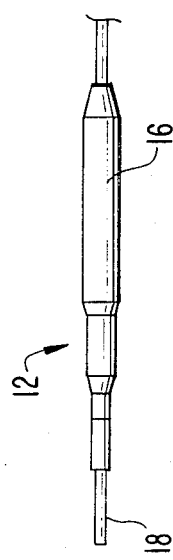
FIG. 1A PRIOR ART
FIG. 1B PRIOR ART
FIG. 2 PRIOR ART

REMOVABLE SLEEVE ADAPTOR FOR ELECTRODE LEADS

BACKGROUND OF THE INVENTION

1. Field of the Invention

The present invention relates to the field of implantable electrode leads for delivering electric stimuli from a pulse generator to body tissue and, more particularly, to an adaptor sleeve for a proximal end of such a lead so as to permit connection to pulse generators having sockets of differing sizes.

2. The Prior Art

In the medical electronics industry, particularly the pacing industry, implantable electrode leads are used for delivering electric stimuli from a pulse generator to body tissue. As illustrated in FIG. 1, an electrode 10 has a proximal end 12 for connection to a pulse generator (not shown) and a distal end 14 for being positioned in the desired body tissue. Proximal end 12 has a plug 16, which includes a conducting pin 18, for insertion into a corresponding socket (not shown) of the pulse generator.

In addition to maintaining electrical contact between pin 18 and the pulse generator, an important function of plug 16 is providing secure mechanical coupling to the pulse generator socket. At present, however, there are no standards regulating the size of the plugs and sockets used for these purposes. Generally, the sizes fall into one of two types—large diameter or small diameter. The former is also known in the art as a "high profile" type whereas the latter is known as a "low profile" type.

In an effort to provide compatibility with a wide range of pulse generators having sockets of different sizes, adaptors have been developed for the proximal ends of electrode leads. A typical adaptor, as shown in FIG. 1 and designated by reference character 20, comprises a simple silicone molding fitted over a "low profile-type" plug 16 so as to make the plug resemble a "high profile-type". Thus, a low profile proximal plug can be adapted to fit the socket of a pulse generator designed to accept larger high profile type plugs. The adaptor is conveniently provided with sealing rings and other features associated with proximal plugs and, to ensure internal sealing between the adaptor and proximal plug, suitable sealing rings are provided on the inside of the adaptor or outside of the smaller proximal plug or both.

For practical reasons, electrode leads can be provided with adaptors already fitted on the proximal end, the adaptor being removed at the discretion of the operating physician should the socket of the pulse generator being implanted so require. Removable adaptor sleeves presently known in the art can generally be classified in one of two categories: thin walled adaptors that can be rolled off the proximal plug or rigid type adaptors that are pulled off the plug. FIG. 2 is an example of a thin walled adaptor 22 showing how its end is rolled up so as to remove it from proximal plug 16. FIG. 3 illustrates a rigid type adaptor 24 which includes a reinforced section 26 permitting the physician's fingers to firmly grasp and remove adaptor 24 from proximal plug 16.

Both categories of adaptors suffer from problems, however. Thin walled adaptors (FIG. 2) are typically pre-fitted to the electrode lead; however, removal of such adaptors so as to fit a low profile socket can frequently be difficult due to the resistance of the adaptor to the necessary rolling action. The thicker walled adaptors (FIG. 3) are typically provided as a separate item subsequently fitted over the lead in the operating room by the physician or nurse so as to fit a high profile socket. These are difficult to fit without a lubricant, however, due to the necessary close tolerance with the proximal plug and the internal sealing rings.

A need therefore exists for an adaptor sleeve which is easy to use and can be removed quickly and safely.

SUMMARY OF THE INVENTION

Accordingly, it is an object of the invention to provide an adaptor sleeve for a proximal plug of an electrode lead so as to accommodate pulse generator sockets of various sizes.

A further object of the invention is an adaptor sleeve that can easily be removed from the proximal plug.

Another object of the invention is an adaptor sleeve which, although easily removed, nevertheless provides secure mechanical and electrical coupling when in place on the proximal plug.

To achieve the objects and in accordance with the purpose of the invention, as embodied and as broadly described herein, an adaptor for a plug end of an electrode lead, the adaptor causing the plug end to have a first diameter and being removable to cause the plug end to have a second diameter, comprises: a sleeve coaxially fitted over the plug end of the electrode lead and having a plurality of axial grooves, the sleeve being removed from the plug end by tearing along at least one of the grooves.

The accompanying drawings illustrate presently preferred embodiments of the invention and, together with the description, serve to explain the principles of the invention.

BRIEF DESCRIPTION OF THE DRAWINGS

FIGS. 1A and 1B are elevational views of an electrode lead with and without an adaptor sleeve, respectively;

FIG. 2 is a cross-sectional view of a conventional thin-walled adaptor being peeled off;

DESCRIPTION OF THE PREFERRED EMBODIMENT

Figure 3:
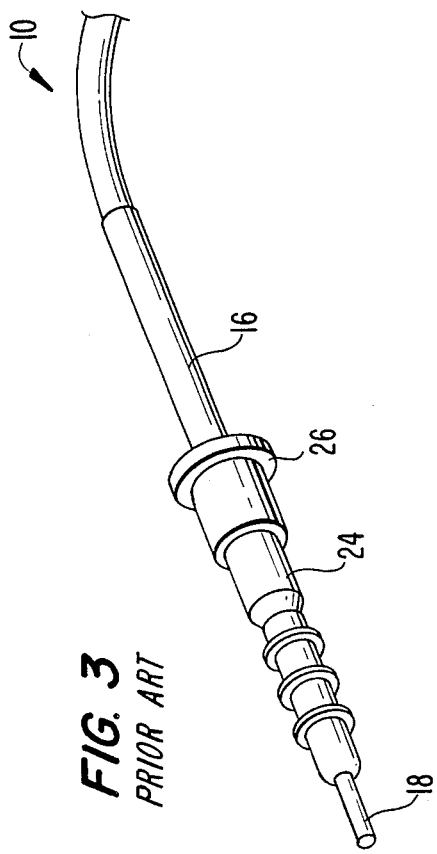
FIG. 3 is a perspective view of a conventional rigid-type adaptor.

Reference will now be made in detail to the presently preferred embodiments of the invention, examples of which are illustrated in the accompanying drawings.

Throughout the drawings, like reference characters are used to designate like elements.

Figure 4A:
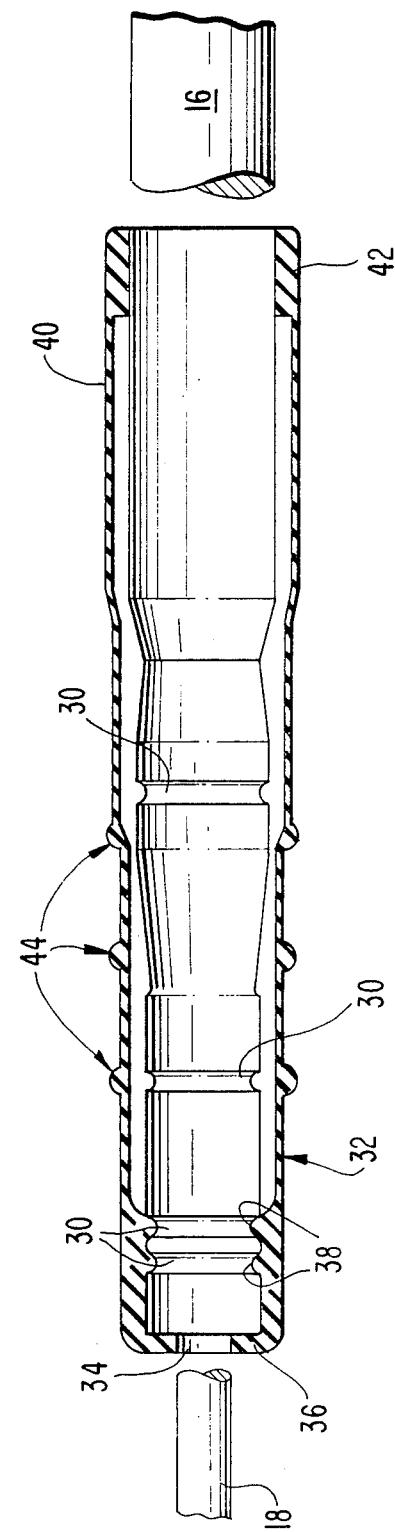
FIG. 4A is a sectioned side elevation view of an adaptor sleeve according to the present invention.
Figure 4B:
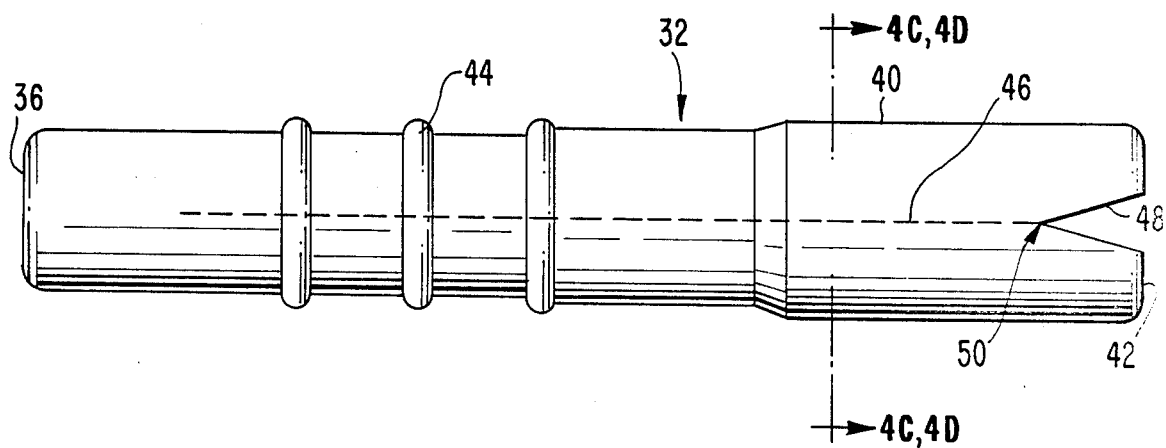
FIG. 4B is a side elevation view of the adaptor sleeve of FIG. 4A.
Figure 4C:
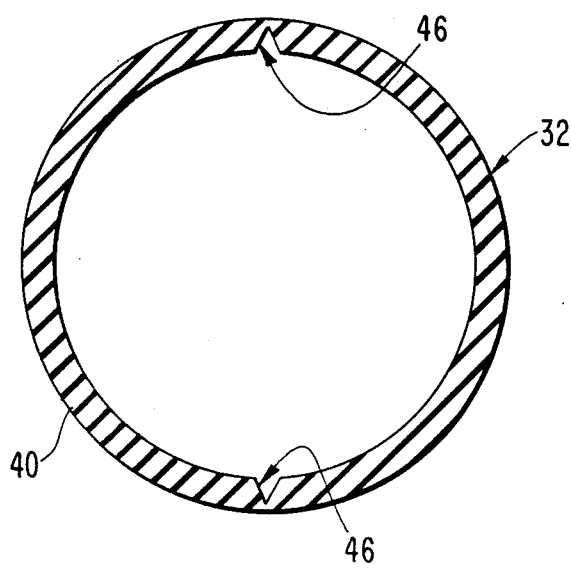
FIG. 4C is a cross-sectional end view of a first embodiment of the adaptor sleeve of FIG. 4A.

FIGS. 4A–4C illustrate an adaptor sleeve 12 constructed according to the present invention. Referring first to FIG. 4A, the plug end of an electrode lead can be seen, including a proximal plug 16 terminating with a forwardly-extending proximal pin 18. According to known design, plug 16 is configured so as to provide secure connection with a pulse generator, such as a pacemaker, by inserting the terminal pin 18 and body of plug 16 into a corresponding socket in the generator.

Plug 16 is of a small diameter, i.e., a "low profile" design. Thus, while plug 16 is suitable for use with pulse generators having similar low-profile sockets, the plug will not provide suitable mechanical and/or electrical coupling with a pace generator having a large or higher profile socket. To provide for compatibility between a low profile plug 16 and a high profile socket (not shown), an adaptor sleeve constructed according to the present invention is provided.

According to the invention, a sleeve is provided coaxially fitted over the plug end of an electrode lead, and having a plurality of axial grooves, the sleeve being removed from the plug end by tearing along at least one of the grooves. As embodied herein, the sleeve is generally designated in FIGS. 4 and 5 by reference character 32. The sleeve 32 is preferably formed of medical grade silicone, polyurethane or similar material, all having good tear resisting properties. The sleeve 32 is formed over the end of proximal plug 16, as shown in FIG. 4A, such that proximal pin 18 protrudes through a corresponding hole 34 in a front wall 36 of sleeve 32. In this manner, proximal pin 18 and plug 16 can be securely inserted into a high profile socket (not shown) of a pulse generator due to the larger diameter provided by the use of sleeve 32.

Sleeve 32 can be heat molded and slid over plug 16 of the electrode lead or affixed by any other suitable manner. To provide secure mechanical coupling between sleeve 32 and plug 16, such as against ingress of fluids, sleeve 32 can be provided with internal guide rings 38 and 30. Thus, any fluid entering through hole 34 and grooves 46 is adequately blocked by the interaction of rings 38 and the body (not shown) of the "low profile" plug 16.

Sleeve 32 includes a side wall 40 on which is provided a plurality of outer sealing rings 44. These rings are intended to co-act with a high profile socket (not shown) so as to provide sealing engagement between plug 16 with adaptor 32 and the socket. The configuration of such rings 44 so as to accomplish this function is well known in the art and need not be explained further.

Sleeve 32 also includes a rear wall 42 which comprises a flap like portion part of side wall 40. This portion comprising rear wall 42 helps to provide easy removal of sleeve 32 from plug 16 in a manner described below.

FIG. 4B illustrates details of axial grooves of an adaptor sleeve 32 constructed according to the invention. As illustrated in this figure, one of the axial grooves is shown and generally designated by reference character 46. Grooves 46 extend axially along side wall 40 of sleeve 32 from substantially the rear wall 42 up through the region of outer sealing rings 44. The preferred termination of axial grooves 46 occurs substantially in the region of inner guide rings 30 (FIG. 4A) since, should the grooves 46 extend further, sealing rings 38 would not operate properly. Various arrangements for axial grooves 46 may be employed within the spirit and scope of the invention, provided the integrity of sealing rings 38 is preserved against ingress of fluid. For example, grooves 46 may be cut through side wall 40 of sleeve 32, in which case the grooves should not extend beyond the left-most one of rings 38. Alternately, grooves 46 may be formed without cutting entirely through side wall 40, thus presenting an effective tear line for removal of sleeve 32 while protecting against ingress of fluids. In this latter case, grooves 46 may extend up to and even farther than rings 38.

According to the preferred embodiment, rear wall 42 of sleeve 32 is provided with notches 48, each notch 48 having an apex 50 which is aligned with one of the axial grooves 46. Preferably, a notch 48 is provided for each axial groove 46. Notches 48 are preferably V-shaped, as illustrated in FIG. 4B, but may also be cut of other shapes without departing from the spirit or scope of this invention.

Figure 4D:
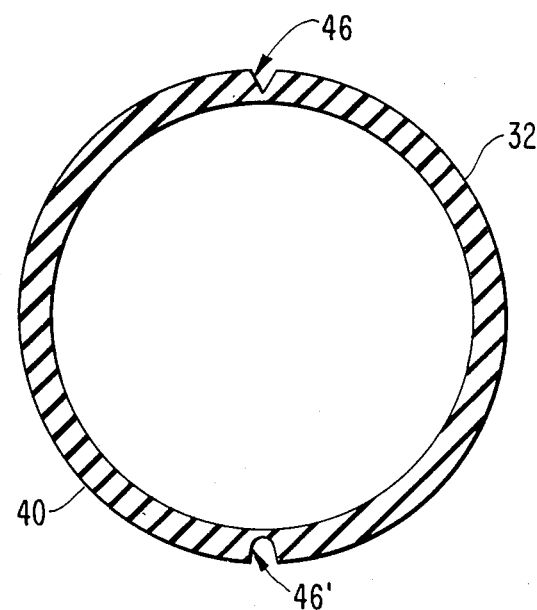
FIG. 4D is a second embodiment of the adaptor sleeve of FIG. 4A.

FIGS. 4C and 4D illustrate details of axial grooves 46 in an adaptor sleeve 32 constructed according to the invention. In the first embodiment, grooves 46 are on an inner surface of sidewall 40 and are V-shaped in cross-section. Preferably, two axial grooves 46 (FIG. 4B) are provided, the grooves being oppositely disposed from each other on the inner surface of sidewall 40. FIG. 4D illustrates a second embodiment on which the axial grooves 46 are located on the outer surface of wall 40. In a further embodiment, the axial grooves may be formed on a generally U-shaped cross-section as designated by reference character 46' in FIG. 4D. The precise shape of the axial grooves is not an essential aspect of the present invention.

Additionally, while the preferred embodiment includes grooves which extend in a linear fashion from rear wall 42 proximate the forward end of adaptor 32, it should be appreciated that the term "axial" as used herein encompasses other grooves which generally extend from wall 42 forward, even in a nonlinear manner. That is, the grooves could have lateral deviations, spirals, angles and the like, so long as the grooves nevertheless provide a weakened portion along the length of side wall 40 to facilitate splitting of the side wall and removal of the adaptor.

Figure 5:
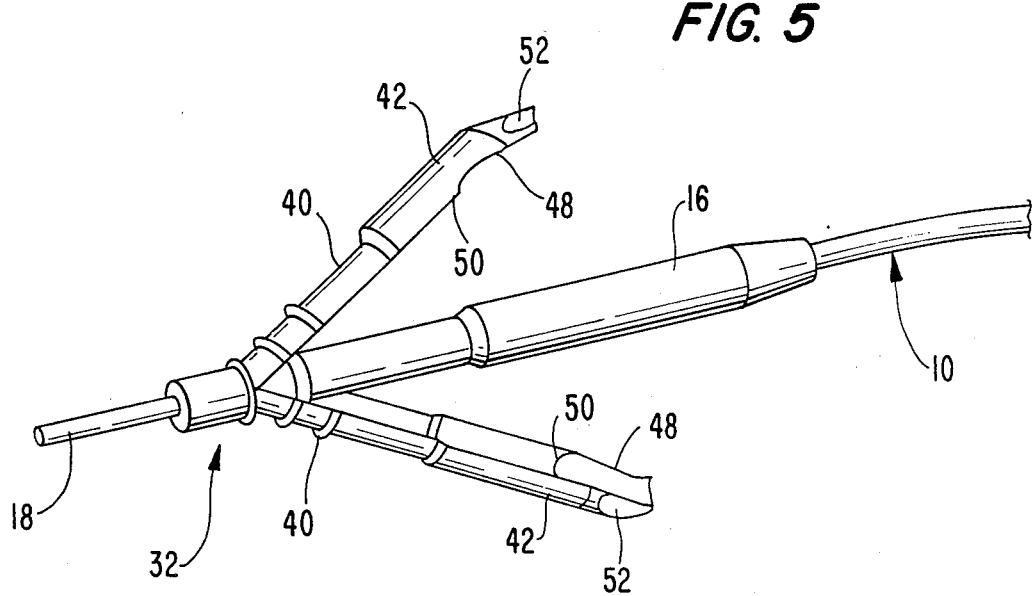
FIG. 5 is a perspective view showing removal of the adaptor sleeve of the present invention from an electrode lead.

The operation of removing adaptor sleeve 32 from the plug end of an electrode lead can best be understood by reference to FIG. 5. When it is determined that the pulse generator being used necessitates a low profile plug rather than high profile arrangement provided by sleeve 32, sleeve 32 can be removed by applying pressure to notch 48 by pulling apart rear walls 42. Such pressure is translated into a tearing or peeling action focused along axial grooves 46 so as to cause sidewalls 40 to split apart, as illustrated in FIG. 5. Since the axial grooves do not extend into the region of adaptor 32 beyond the inner sealing rings (not shown), the entire adaptor can be removed as a unitary piece. This exposes low profile plug 16 for connection with the corresponding socket of the pulse generator (not shown).

From the foregoing, it can be appreciated that the present invention provides an adaptor for connecting an electrode lead to a pulse generator of either a low profile or high profile socket configuration. The adaptor can be affixed to the electrode lead during manufacture and, thereafter, readily removed in the field. Ease of removal of the adaptor is provided by the axial grooves in the sidewall of the adaptor sleeve. While the preferred number of grooves is two, additional grooves may be employed without departing from the spirit or scope of this invention.

It will be apparent to those skilled in the art that modifications and variations can be made in the adaptor sleeve of this invention. The invention in its broader aspects is, therefore, not limited to the specific details, representative methods and apparatus, and illustrative examples shown and described hereinabove. Thus, it is intended that all matter contained in the foregoing description or shown in the accompanying drawings shall be interpreted as illustrative and not in a limiting sense.

What is claimed is:

1. An adaptor for a plug end of an electrode lead, the adaptor causing the plug end to have a first diameter and being removable to cause the plug end to have a second, smaller, diameter, comprising:
    a sleeve coaxially fitted over the plug end of the electrode lead and having a plurality of axial grooves, said sleeve being removed from the plug end by tearing along at least one of said grooves.

2. An adaptor as recited in claim 1, wherein said plurality of axial grooves are disposed on an inside surface of said sleeve.

3. An adaptor as recited in claim 2, wherein one end of said sleeve has a notch that is aligned with one of said plurality of grooves.

4. An adaptor as recited in claim 2, wherein one end of said sleeve has a plurality of notches, each one of said plurality of grooves having one of said plurality of notches substantially aligned therewith.

5. An adaptor as recited in claim 2, wherein said grooves are V-shaped in cross section.

6. An adaptor as recited in claim 2, wherein said grooves are U-shaped in cross section.

7. An adaptor as recited in claim 1, wherein said plurality of axial grooves are disposed on an outer surface of said sleeve.

8. An adaptor as recited in claim 8, wherein one end of said sleeve has a notch that is aligned with one of said plurality of grooves.

9. An adaptor as recited in claim 7, wherein one end of said sleeve has a plurality of notches, each one of said plurality of grooves having one of said plurality of notches substantially aligned therewith.

10. An adaptor as recited in claim 7, wherein said grooves are V-shaped in cross section.

11. An adaptor as recited in claim 7, wherein said grooves are U-shaped in cross section.

12. An electrode lead assembly for delivering electrical stimuli from a pulse generator to body tissue, comprising:
    an electrode lead having a proximal end for insertion into a corresponding socket of the pulse generator; and
    a sleeve coaxially fitted over the proximal end of the electrode lead, said sleeve having a plurality of axial grooves along which tearing can occur so as to remove said sleeve from the electrode lead, the electrode lead with said sleeve fitting a pulse generator socket of a first size and the electrode lead without said sleeve fitting a pulse generator socket of a second, smaller size.

13. An electrode lead assembly as recited in claim 12, wherein said grooves are disposed on an inner surface of said sleeve.

14. An electrode lead assembly as recited in claim 13, wherein said sleeve has a proximal end and a distal end, the distal end of said sleeve having a plurality of notches, each one of said plurality of grooves having one of said plurality of notches substantially aligned therewith.

15. An electrode lead assembly as recited in claim 12, wherein said grooves are disposed on an outer surface of said sleeve.

16. An electrode lead assembly as recited in claim 15, wherein said sleeve has a proximal end and a distal end, the distal end of said sleeve having a plurality of notches, each one of said plurality of grooves having one of said plurality of notches substantialy aligned therewith.

* * * * *